US012059572B2

(12) United States Patent
Mueller et al.

(10) Patent No.: US 12,059,572 B2
(45) Date of Patent: Aug. 13, 2024

(54) IMPLANTABLE ULTRASONIC DEVICE

(71) Applicant: Medtronic, Inc., Minneapolis, MN (US)

(72) Inventors: Jerel K. Mueller, Saint Paul, MN (US); Sarah J. Offutt, Golden Valley, MN (US); Jamu K. Alford, Ham Lake, MN (US); Douglas S. Cerny, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 351 days.

(21) Appl. No.: 17/439,039

(22) PCT Filed: Mar. 25, 2020

(86) PCT No.: PCT/US2020/024690
§ 371 (c)(1),
(2) Date: Sep. 14, 2021

(87) PCT Pub. No.: WO2020/219202
PCT Pub. Date: Oct. 29, 2020

(65) Prior Publication Data
US 2022/0152402 A1    May 19, 2022

Related U.S. Application Data

(60) Provisional application No. 62/838,685, filed on Apr. 25, 2019.

(51) Int. Cl.
*A61N 1/05*    (2006.01)
*A61N 1/36*    (2006.01)
(Continued)

(52) U.S. Cl.
CPC ......... *A61N 1/3787* (2013.01); *A61N 1/0504* (2013.01); *A61N 1/0558* (2013.01); *A61N 1/36153* (2013.01); *A61N 1/37205* (2013.01)

(58) Field of Classification Search
CPC .. A61N 1/3787; A61N 1/0504; A61N 1/0558; A61N 1/36153; A61N 1/37205;
(Continued)

(56) References Cited

U.S. PATENT DOCUMENTS 6,735,474 B1    5/2004   Loeb et al.
2011/0301670 A1*  12/2011   Gross ................. A61N 1/36171
                                                      607/2

(Continued)

FOREIGN PATENT DOCUMENTS

WO    2013176744 A1    11/2013
WO    2015196164 A2    12/2015

OTHER PUBLICATIONS

International Search Report and Written Opinion dated Jun. 26, 2020, for corresponding International Application No. PCT/US2020/024690; International Filing Date: Mar. 25, 2020 consisting of 16-pages.

(Continued)

*Primary Examiner* — Ankit D Tejani
*Assistant Examiner* — Joshua Brendon Solomon
(74) *Attorney, Agent, or Firm* — Shumaker & Sieffert, P.A.

(57) ABSTRACT

An implantable electrical stimulation device including an implant sized and configured to be implanted subcutaneously, the implant being configured to rectify a received pulse train of ultrasound into a single electrical pulse configured to stimulate a tibial nerve of a patient.

18 Claims, 4 Drawing Sheets

(51) Int. Cl.
*A61N 1/372* (2006.01)
*A61N 1/378* (2006.01)
(58) Field of Classification Search
CPC .............. A61N 1/36007; A61N 1/3606; A61N 1/37217
See application file for complete search history.

(56) References Cited

U.S. PATENT DOCUMENTS

| | | |
|---|---|---|
| 2014/0058292 A1 | 2/2014 | Alford et al. |
| 2014/0163580 A1* | 6/2014 | Tischendorf ......... A61N 1/3727 607/116 |
| 2015/0148878 A1 | 5/2015 | Yoo et al. |
| 2017/0319858 A1 | 11/2017 | Radziemski et al. |
| 2019/0150884 A1* | 5/2019 | Maharbiz ................. A61B 8/48 |

OTHER PUBLICATIONS

Radziemski, Leon, Makin, Inder Raj S., In Vivo Demonstration of Ultrasound Power Delivery to Charge Implanted Medical Devices Via Acute and Survival Studies, Elsevier, Ultrasonics 64 (2016) 1-9, http://dx.doi.org/10.1016/j.ultras.2015.07.012.

* cited by examiner

| ELECTRICAL OUTPUT PARAMETER | MINIMUM | MAXIMUM |
|---|---|---|
| Amplitude<br>Assumes sufficient coupling and typical depth (0.5 to 3 cm depth) with roughly 1kΩ tissue impedance | 0V | 10V |
| Pulse Width | 20 μsec | 400 μsec |
| Rate | 10Hz | 10kHz |

# IMPLANTABLE ULTRASONIC DEVICE

CROSS-REFERENCE TO RELATED APPLICATIONS

This application is a Submission under 35 U.S.C. § 371 for U.S. National Stage Patent Application of, and claims priority to, International Application Number PCT/US2020/024690, entitled IMPLANTABLE ULTRASONIC DEVICE, filed Mar. 25, 2020, which is related to and claims priority to U.S. Provisional Patent Ser. No. 62/838,685 filed Apr. 25, 2019, the entirety of all of which are incorporated herein by reference.

TECHNICAL FIELD

The present technology is generally related to implantable ultrasonic devices and delivery of electrical energy to the nervous system.

BACKGROUND

Urinary incontinence is the involuntary leakage of urine which may be caused by, for example, loss of control over the urinary sphincter causing an urge to urinate or overflow incontinence. About one-quarter to one-third of men and women in the United States experience urinary incontinence. An estimated 30 percent of females aged 30-60 may suffer from some form of urinary incontinence.

Treatments of urinary incontinence tend to treat symptoms of urinary incontinence and not the cause of the problem, or can require difficult surgeries. For example, methods of treatment include pelvic muscle training, use of absorbent pads, catheters, medications, or surgery, which can either be a source of embarrassment, discomfort, or result in surgical complications.

SUMMARY

The techniques of this disclosure generally relate to devices and methods for stimulating nerves in a patient, and in particular, the tibial nerve.

In one aspect, the present disclosure provides an implantable electrical stimulation device including an implant sized and configured to be implanted subcutaneously, the implant being configured to rectify a received pulse train of ultrasound into a single electrical pulse configured to stimulate a tibial nerve of a patient.

In another aspect, the implant further includes a fixation element configured to retain the implant in a position proximate the tibial nerve.

In another aspect, the fixation element is transitionable from a first position during deployment to a second position during subcutaneous fixation.

In another aspect, the fixation element includes a plurality of tines.

In another aspect, the implant defines an interior, and wherein the implant includes a circuit board having a processing circuity, an inductive coil, and a plurality of piezoelectric elements disposed within the interior of the implant and in communication with each other to rectify the received pulse train of ultrasound into a single electrical pulse.

In another aspect, the implant further includes an electrode configured to conduct the single electrical pulse to the tibial nerve.

In another aspect, the implant is passively powered.

In another aspect, the implant is configured to output a voltage having an amplitude up to 20V for the single electrical pulse.

In one aspect, a method for treating urinary incontinence includes subcutaneously implanting an implant proximate a tibial nerve of a patient, the implant being configured to rectify a received pulse train of ultrasound into a single electrical pulse configured to stimulate the tibial nerve of the patient, and delivering a pulse train of ultrasound to the implant and electrically stimulating the tibial nerve.

In another aspect, subcutaneously implanting the implant includes piercing skin proximate an ankle of the patient and stimulating a target area for implantation of the implant with a stimulation device to determine a suitable location for implantation of the implant.

In another aspect, subcutaneously implanting the implant fixating the implant with subcutaneous fascia.

In another aspect, wherein delivering a pulse train of ultrasound to the implant includes delivering ultrasound from an ultrasound patch adhered to the surface of skin of the patient.

In one aspect, a system for stimulating a tibial nerve of a patient includes an implant delivery device, the implant delivery device being configured to deliver an implant subcutaneously proximate the tibial nerve, the implant being configured to rectify a received pulse train of ultrasound into a single electrical pulse configured to stimulate the tibial nerve of the patient. An ultrasound device coupled to the skin of the patient and configured to deliver the pulse train of ultrasound to the implant is included.

In another aspect, the implant delivery device is configured to stimulate a target area for implantation of the implant with a stimulation device to determine a suitable location for implantation of the implant.

In another aspect, the implant delivery device includes a needle defining a lumen therein, and wherein the implant is slideably disposed within the lumen.

In another aspect, the implant further includes a fixation element configured to retain the implant in a position proximate the tibial nerve.

In another aspect, the fixation element is transitionable from a first position during deployment to a second position during subcutaneous fixation.

In another aspect, the fixation element includes a plurality of tines.

In another aspect, the implant defines an interior, and wherein the implant includes a circuit board having a processing circuity, an inductive coil, and a plurality of piezoelectric elements disposed within the interior of the implant, the plurality of piezoelectric elements being configured rectify the received pulse train of ultrasound into a single electrical pulse.

In another aspect, the implant further includes an electrode configured to conduct the single electrical pulse to the tibial nerve.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
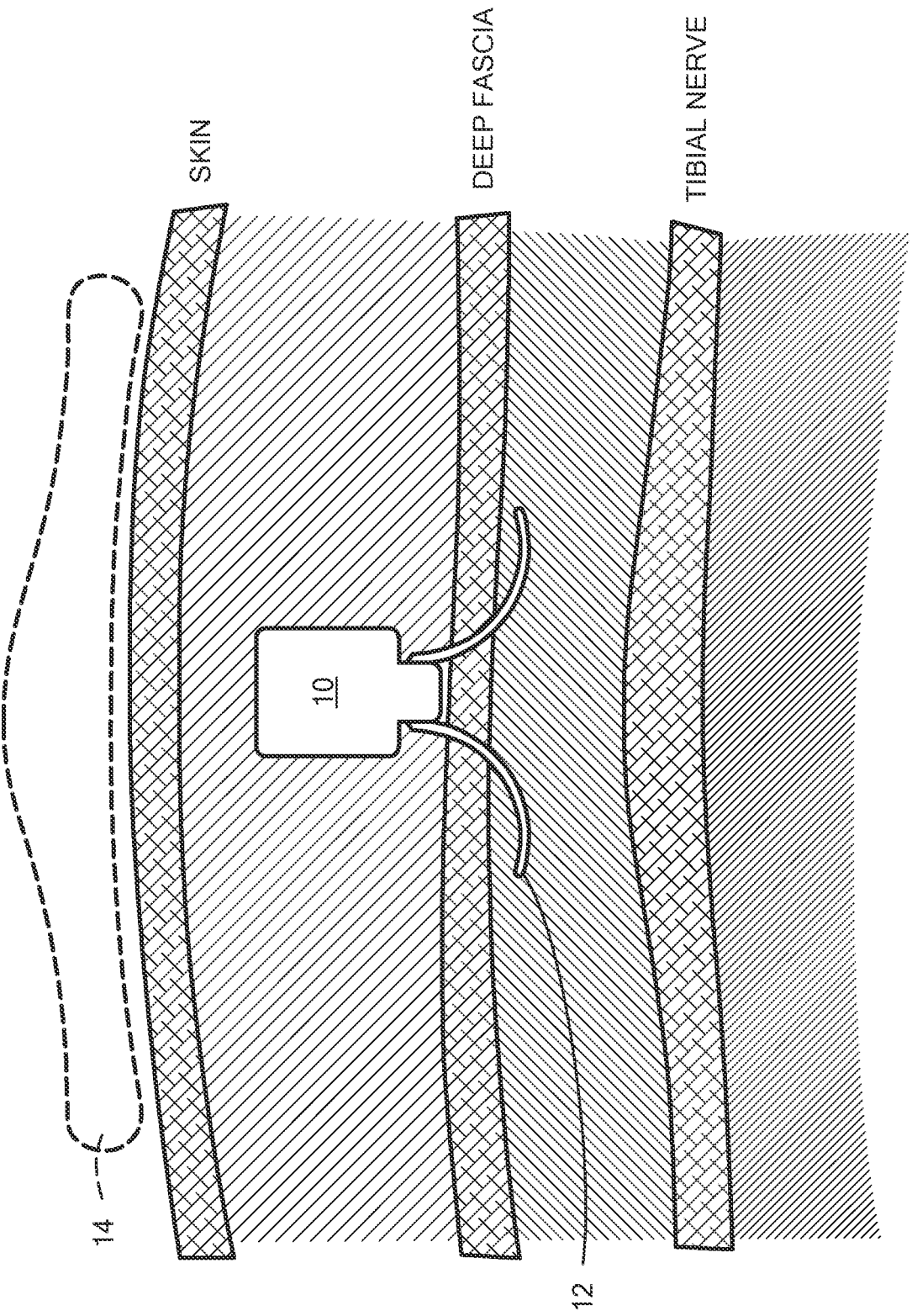
FIG. 1 is a cross-sectional schematic view of an exemplary implanted subcutaneous electrical stimulation device.

Referring now to the drawings in which like reference designators refer to like elements, there is shown in FIG. 1 an exemplary implant constructed in accordance with the principles of the present application and designated generally a "10." The implant 10 may be sized and configured to be implanted subcutaneously, for example, underneath a human or animal patient's skin by ankle, thigh, pelvis, and the like. In one configuration, the implant 10 is sized to be implanted within subcutaneous fascia proximate the tibial nerve. For example, as shown in FIG. 1, the implant may include a fixation element 12 configured to affix and retain the implant 10 within a target subcutaneous area. The fixation element 12 may include, but is not limited to, a plurality of tines, which may be composed of flexible and/or shape memory material such as Nitinol, or barbs, hooks, hook and loop fasteners, or other anchors. In one configuration, the fixation element is transitionable from a first position during deployment from a position outside the body to a second position during subcutaneous fixation. For example, the fixation element 12 may transition from a position during insertion in which the plurality of tines is substantially parallel with a major axis of the implant 10, to a position in which the plurality of tines extends in a direction substantially orthogonal to the major axis of the implant. In the configuration shown in FIG. 1, the plurality of tines extends into the deep fascia to prevent migration of the implant 10.

The implant 10 may be configured to rectify a received pulse train of ultrasound into a single electrical pulse configured to stimulate a tibial nerve of a patient, as discussed in more detail below. For example, as shown in FIG. 1, an ultrasound patch 14 may be adhered or otherwise positioned on the skin proximate the implant 10 to deliver ultrasound underneath the skin and to the implant 10 including pulse trains of ultrasound. In other configurations, other ultrasound devices may be used to deliver ultrasound to the implant 10.

Figure 2:
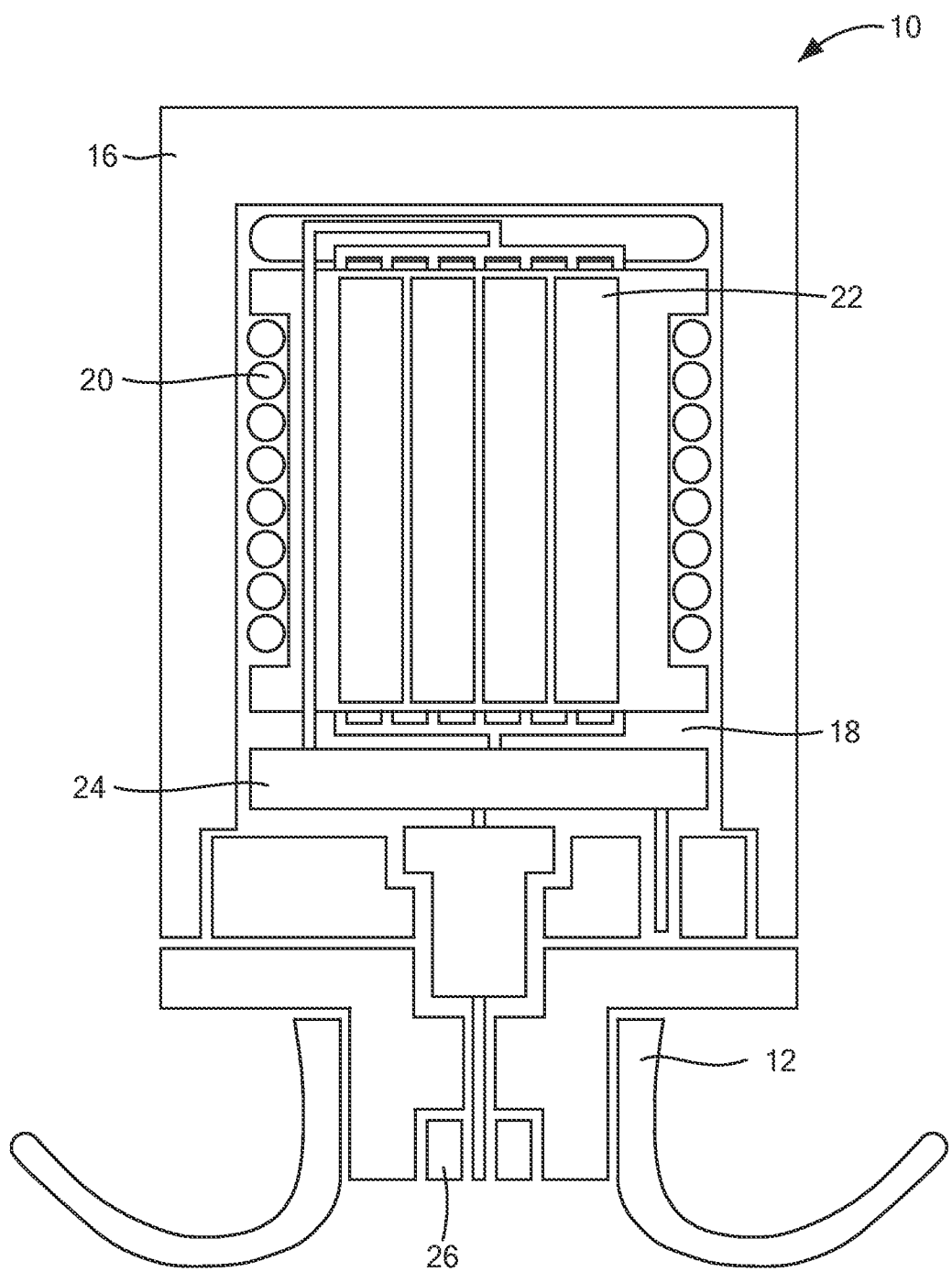
FIG. 2 is a cross-sectional schematic view of the electrical stimulation device shown in FIG. 1.

Referring now to FIG. 2, the implant 10 may include a housing 16 sized and configured to retain the various components of the implant. The housing 16 may further define an interior 18 sized to receive an inductive coil 20 for communication with the device 14 and a plurality of piezoelectric elements 22, such as PZT rods. The piezoelectric elements 22 are configured to rectify ultrasound pulses into electrical pulses for stimulation of nerves, and in particular, the tibial nerve of the patient. The implant 10 may further include a circuit board 24 having processing circuitry configured to control operation of the implant 10 to rectify received pulse trains of ultrasound. In one configuration, the implant includes its own rechargeable power source (not shown) or passively powered by the ultrasound device 14. The configuration of the implant 10 shown in FIG. 2 is merely an exemplary arrangement of the components disposed therein and other configurations are contemplated by this disclosure. In one configuration, one or more electrodes 26 are in communication with the circuit board 24, the plurality of piezoelectric elements 22 and the inductive coil to deliver the rectified electrical waveform to target nerve, for example, the tibial nerve. In the configuration shown in FIG. 2, the electrode 26 is cylindrical and is coupled to the distal end of the implant between the fixation elements 12.

Figures 3, 4:
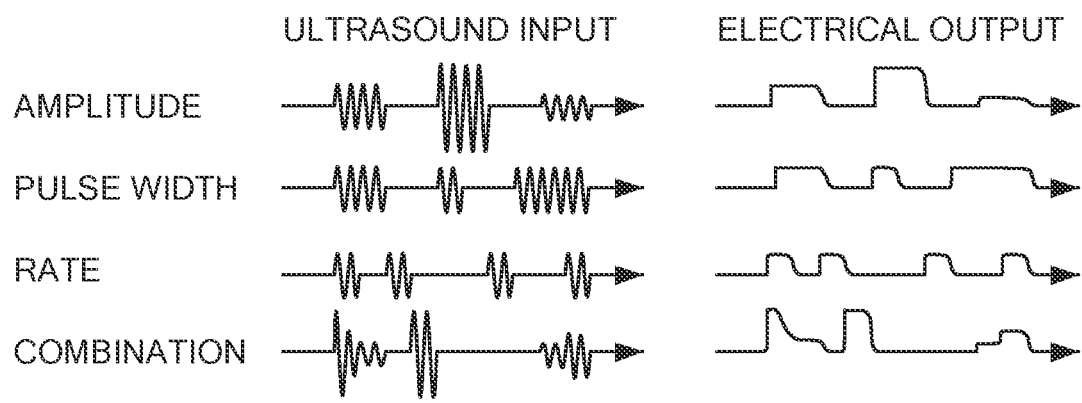
FIG. 3 is a chart showing the rectification of exemplary ultrasound inputs into electrical outputs by the implant shown in FIG. 2.
FIG. 4 is a chart shown exemplary electrical output parameters of the implant shown in FIG. 2.

Referring now to FIGS. 3 and 4, in one configuration, the implant 10 is configured to output an electrical waveform having a minimum of 0V to a maximum of 10V assuming sufficient coupling of the ultrasound device 14 to the implant 10 and a depth of approximately 0.5 to 3 cm insertion of the implant subcutaneously with about 1 kOhm tissue impedance. In other configurations, the implant 10 may output waveforms of various other amplitudes depending on the depth of insertion of the implant and the tissue impedance. For example, the maximum output of the implant 10 may be up to 20V. In one configuration, a pulse width of an outputted electrical waveform may range, for example, between 20 microseconds to 400 microseconds and between a frequency of 10 Hz to 10 kHz. FIG. 3 shows examples of some ultrasound waveform inputs received by the implant and the corresponding rectified electrical waveform outputs.

Figure 5:
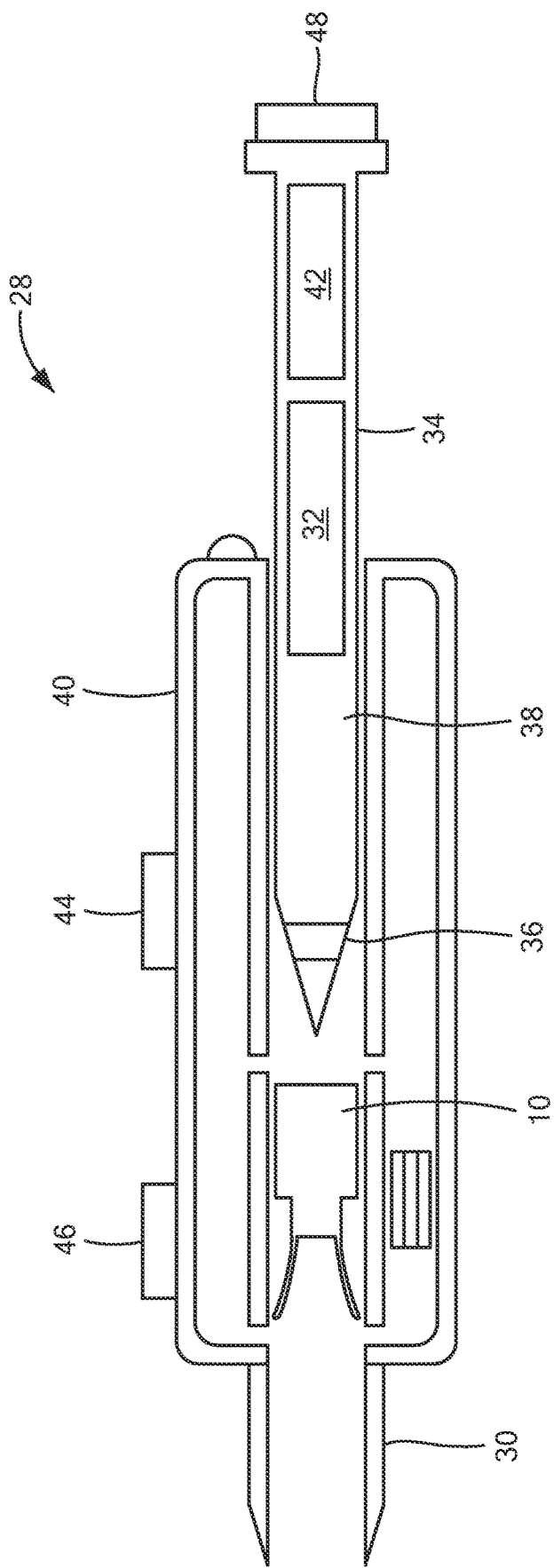
FIG. 5 is a cross-sectional schematic view of an exemplary system for implanting the implant shown in FIG. 2.

Referring now to FIG. 5, an exemplary implant delivery device 28 is configured to pierce, cut, or otherwise penetrate the skin of the patient for delivery and implantation of the implant 10. In one configuration, the device 28 may include a needle, tube, or other piercing element 30 at its distal end and configured to pierce the skin and create an opening for delivery of the implant 10. In one configuration, the piercing element 30 is hollow and sized to slidably receive the implant 10, and in other configurations may be solid. The device 28 may further include an electrical stimulation element 32 configured to electrically test a target area of treatment to determine a suitable location for the implant 10. In particular, the stimulation element 32 may include a stimulation engine 34 in communication with an electrode 36 configured to apply a test electrical pulse to stimulate the target implant area to determine if, for example, the tibial nerve is stimulated. If the tibial nerve is stimulated, the implant 10 is implanted at the location where stimulation is observed. The test level pulse may be less than or equal to a therapeutic electrical pulse delivered by the implant 10 to the tibial nerve. In one configuration, the device 28 includes a plunger 38 slidably received within a housing 40 to advance the test electrode 36 toward the target tissue region. In one configuration, the stimulation engine 34 and one or more batteries 42 may be disposed within the plunger 38 and in other configurations may be disposed elsewhere within or to device 28. In the configuration shown in FIG. 5, the device 28 includes a retractor actuator 44 configured advance and retract the plunger 38 within the housing 40, a stimulation actuator 46 to start and stop the stimulation engine 32, and an amplitude control actuator 48 to control the amplitude of the test level stimulation.

In an exemplary use of the device 28, the user may pierce the skin of the patient in a location in which the tibial nerve may be accessed, for example, by the ankle or other portion of the leg. A target area for implantation of the implant 10 is electrically stimulated with the stimulation device 32 to determine a suitable location for implantation of the implant 10. The implant 10 is then implanted at the suitable location. In one configuration the device 28 implants the implant 10 only and in other configurations a separate device (not shown) may be used to pierce the skin, or vice versa. In the configuration shown in FIG. 5, the implant is disposed proximal to tube 30 within the housing 40. The implant 10 may be side-loaded into the housing 40 and positioned distal to the distal end of plunger 38. The plunger 38 is advanced distally within the housing 40 and pushes on the implant 10 to advance the implant out from the housing 40. It is further contemplated that piercing the patient's skin and implanting the implant 10 may be achieved through separate medical devices.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An implantable electrical stimulation device, comprising:
   a housing sized and configured to be implanted subcutaneously;
   an inductive coil disposed within the housing and;
   a plurality of piezoelectric elements disposed within the housing and in communication with each other to rectify a received pulse train of ultrasound into a single electrical pulse to stimulate a tibial nerve of a patient, wherein the piezoelectric elements are surrounded by turns of the inductive coil.

2. The device of claim 1, further comprises a fixation element configured to retain the implantable electrical stimulation device in a position proximate the tibial nerve.

3. The device of claim 2, wherein the fixation element is transitionable from a first position during deployment to a second position during subcutaneous fixation.

4. The device of claim 2, wherein the fixation element includes a plurality of tines.

5. The device of claim 1, further comprising at least one electrode configured to conduct the single electrical pulse to the tibial nerve.

6. The device of claim 1, wherein the implantable electrical stimulation device is configured to be passively powered.

7. The device of claim 1, wherein the implantable electrical stimulation device is configured to output a voltage having an amplitude up to 20V for the single electrical pulse.

8. A method for treating urinary incontinence, comprising:
   delivering, from an external ultrasound device, a pulse train of ultrasound to tissue of a patient;
   receiving, by a plurality of piezoelectric elements disposed within an implant, the pulse train of ultrasound, wherein the plurality of piezoelectric elements are surrounded by turns of an inductive coil within the implant; and
   electrically stimulating the tibial nerve via the plurality of piezoelectric elements rectifying the pulse train of ultrasound into a single electrical pulse delivered by the implant.

9. The method of claim 8, further comprising subcutaneously implanting the implant proximate the tibial nerve by at least piercing skin proximate an ankle of the patient and stimulating a target area for implantation of the implant with a stimulation device to determine a suitable location for implantation of the implant.

10. The method of claim 9, further comprising subcutaneously implanting the implant proximate the tibial nerve by at least fixating the implant with subcutaneous fascia.

11. The method of claim 8, wherein the external ultrasound device is an ultrasound patch, and wherein delivering the pulse train of ultrasound comprises delivering the ultrasound from the ultrasound patch adhered to a surface of skin of the patient.

12. A system for stimulating a tibial nerve of a patient, comprising:
   an implant comprising an inductive coil and a plurality of piezoelectric elements, the plurality of piezoelectric elements configured to rectify a received pulse train of ultrasound into a single electrical pulse to stimulate the tibial nerve of the patient, wherein the piezoelectric elements are surrounded by turns of the inductive coil;
   an implant delivery device configured to deliver the implant subcutaneously proximate the tibial nerve; and
   an ultrasound device coupled to the skin of the patient and configured to deliver the pulse train of ultrasound to the implant.

13. The system of claim 12, wherein the implant delivery device is configured to stimulate a target area for implantation of the implant with a stimulation device to determine a suitable location for implantation of the implant.

14. The system of claim 12, wherein the implant delivery device includes a needle defining a lumen therein, and wherein the implant is slideably disposed within the lumen.

15. The system of claim 12, wherein the implant further includes a fixation element configured to retain the implant in a position proximate the tibial nerve.

16. The system of claim 15, wherein the fixation element is transitionable from a first position during deployment to a second position during subcutaneous fixation.

17. The system of claim 15, wherein the fixation element includes a plurality of tines.

18. The system of claim 12, wherein the implant further includes at least one electrode configured to conduct the single electrical pulse to the tibial nerve.

* * * * *